United States Patent [19]

Jarolics

[11] Patent Number: 4,772,454
[45] Date of Patent: Sep. 20, 1988

[54] PROBE FOR EXTRACTING A GAS SAMPLE FROM A HOT DUSTY GAS FLOW

[75] Inventor: Gyula Jarolics, Copenhagen, Denmark

[73] Assignee: F. L. Smidth & Co. A/S, Copenhagen, Denmark

[21] Appl. No.: 879,207

[22] Filed: Jun. 26, 1986

[30] Foreign Application Priority Data

Aug. 13, 1985 [GB] United Kingdom ............... 8520273

[51] Int. Cl.⁴ .................... G01N 1/22; G01N 31/00
[52] U.S. Cl. ................... 422/101; 422/83; 422/99; 436/181; 73/863.23; 73/864.33
[58] Field of Search ........... 422/99, 101, 83; 436/181; 73/863.23, 864.33

[56] References Cited

U.S. PATENT DOCUMENTS

| | | | |
|---|---|---|---|
| 3,748,905 | 7/1973 | Fletcher et al. | 73/864.33 X |
| 3,972,225 | 8/1976 | Fort et al. | 73/863.23 X |
| 4,014,216 | 3/1977 | Thornton et al. | 73/863.23 |
| 4,139,351 | 2/1979 | Ostertag et al. | 55/97 |
| 4,180,383 | 12/1979 | Johnson | 422/101 X |
| 4,245,571 | 1/1981 | Przewalski | 110/246 |
| 4,277,259 | 7/1981 | Rounbehler et al. | 436/181 X |

FOREIGN PATENT DOCUMENTS 3327180 2/1985 Fed. Rep. of Germany .

Primary Examiner—Michael S. Marcus
Assistant Examiner—Lynn M. Kummert
Attorney, Agent, or Firm—Brumbaugh, Graves, Donohue & Raymond

[57] ABSTRACT

A probe for taking a sample of dusty gas has a duct (2) with a cooling mantle (11) and leading to a compartment (4) with a filter (5). The duct inlet (1) is convergent to reduce gas velocity and hence dust entrainment.

7 Claims, 1 Drawing Sheet

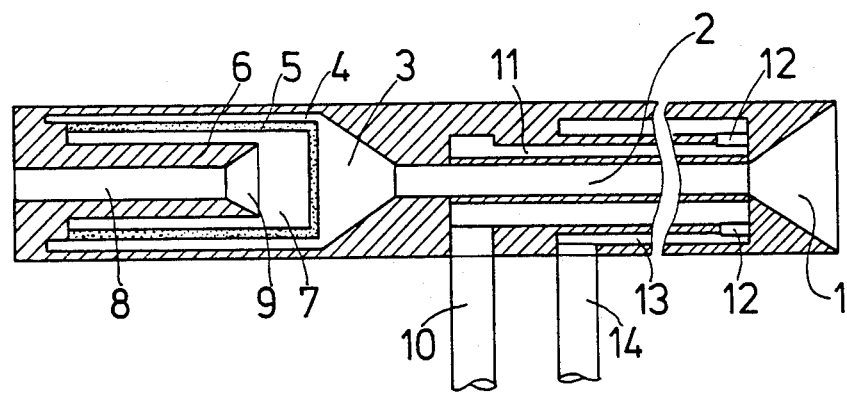

PROBE FOR EXTRACTING A GAS SAMPLE FROM A HOT DUSTY GAS FLOW

The invention relates to a probe for extracting a gas sample from a hot dusty gas flow e.g. from the flue gas of a calciner.

Such a probe must be cooled to stand the hot flue gas and the extracted sample must be filtered to remove dust sucked in with the sample. As it is hardly possible to have a filter which can stand the hot flue gas for a long period, the filter is positioned so that the gas sample is cooled before reaching the filter.

Further, the dust content of the extracted gas must be reduced to prevent fast clogging of the filter.

According to DE-A-No. 3327180 this is achieved by a probe having a cooling mantle through which a cooling medium flows, and having its gas inlets on the side of the probe. When the probe is mounted in the gas flow, from which a sample should be extracted, the gas inlets are placed on the leeward side of the probe.

In connection with fast acting gas monitoring equipment as described in our GB patent application No. 8517549, according to which a gas sample is sucked very quickly by a pump from the probe to an analyzing station, the gas cooled in the probe has a high velocity through the probe and its connection pipe. At the inlet of the probe, the gas sample not yet cooled has a big volume and the gas velocity at the inlet of the probe therefore has to be extremely high, which promotes dust entrainment.

It is therefore an object to provide a probe with a low inlet velocity of the gas and in accordance with the invention, this is achieved by a probe having a duct provided with cooling means and leading from a gas inlet to a filter compartment with a filter, characterized in that the gas inlet is convergent in the direction into the duct.

The convergent, preferably frusto-conical, gas inlet contributes to a reduction in the dust entrainment in the gas, in that the greater the front cross-section of the inlet, the smaller the gas velocity and therefore the smaller the dust entrainment.

In the convergent inlet the gas is accelerated to a higher velocity necessary to prevent precipitation of entrained dust in the duct leading to the filter compartment at the outlet end of the duct.

The transition between the duct and the filter compartment may be divergent, preferably frusto-conical, to enhance the effective removal of dust from the filter and probe duct when intermittant compressed air pulses for cleaning purposes are supplied to the filter in the opposite direction to the sample gas flow.

To minimize the reaction time of the probe the shape of the filter compartment may substantially correspond to the outer shape of a chosen standard filter on the market, leaving only little space between filter and compartment. Further, if the filter has a cavity on its downstream side, a body forming part of a housing of the probe may substantially fill the cavity of the filter.

This body may have a duct ending in at least one nozzle facing the inside of the filter. This duct is used for feeding compressed air to the probe for cleaning the filter. The duct may also be used as a gas outlet from the probe. However, the gas outlet may alternatively be provided by a separate duct leading from the downstream side of the filter.

The new construction of the probe permits the use of only metallic parts, thereby overcoming the disadvantage of differential thermal expansion in systems combining ceramic and metal.

The invention will now be explained in more detail with reference to the accompanying drawing which shows diagrammatically in axial section one example of a probe constructed according to the invention.

In this form the probe appears substantially integral although it may in practice be composed of several parts.

The probe has a convergent cone-shaped gas inlet 1 from which a duct 2 leads via a divergent cone-shaped transition 3 to a filter compartment 4 in which a filter 5 made from sintered metal grains is mounted.

A body 6 forming part of the probe housing fills the greater part of a cavity 7 of the filter 5. The body 6 has an axial outlet duct 8 leading from the cavity of the filter. This duct may serve both as a gas outlet duct and as a duct for feeding compressed air into the filter 5 for cleaning purposes and may therefore have a nozzle 9 at its opening to the cavity 7.

As the object of the probe is to extract hot gas from a gas flow, at least that part which projects into the hot gas flow must be cooled. Further, the extracted gas sample must be cooled before it reaches the filter. This cooling is obtained by feeding a cooling liquid through a pipe 10 to a cylindrical cooling mantle 11 surrounding the duct 2. From the mantle 11 the cooling liquid passes through an opening 12 to a cylindrical cooling duct 13 close to the outer cylindrical surface of the hot part of the probe, and from the duct 13 the cooling liquid leaves the probe through a pipe 14.

Although the extracted gas sample should be cooled to protect the filter 5 it should not be cooled below its dew point as condensation in the duct 2 would be damaging to the functioning of the probe. To avoid condensation in the duct 2 the cooling liquid may therefore be preheated, in a known way and before feeding into the cooling mantle 11, to a temperature above the dew point of the gas sample passing through the duct 2.

I claim:

1. A probe for extracting a gas sample from a hot, dusty gas flow, said probe comprising a duct provided with a cooling means and leading from a gas inlet to a filter compartment with a filter, wherein said gas inlet is convergent from a point of gas entry in the downstream direction such that the cross-sectional area of the gas inlet lessens in the downstream direction thereby causing the gas velocity at the point of gas entry to be lower than the gas velocity in the duct, said probe having a gas outlet downstream of said filter.

2. A probe according to claim 1, wherein said gas inlet is frusto-conical.

3. A probe according to claim 1, wherein all parts of said probe are metallic.

4. A probe according to claim 1, in which a transition between said duct and said filter compartment is divergent in the direction into said filter compartment.

5. A probe according to claim 4, wherein said transition is frusto-conical.

6. A probe according to claim 1 wherein said filter is shaped so as to form a cavity on the downstream side of said filter and communicating with said gas outlet, said filter disposed such that said gas sample passes from said duct, through said filter into said cavity, and then to said gas outlet.

7. A probe according to claim 6 wherein said cavity is substantially filled by a ductcontaining element, said duct in said duct-containing element having at one end at least one nozzle directed at the interior of said cavity for directing compressed air into said cavity for cleaning purposes, said duct having at the other end said gas outlet.

* * * * *